US010589118B2

(12) United States Patent
Schneider

(10) Patent No.: US 10,589,118 B2
(45) Date of Patent: *Mar. 17, 2020

(54) ENHANCED SPATIAL SUMMATION FOR DEEP-BRAIN TRANSCRANIAL MAGNETIC STIMULATION

(71) Applicants: BRAINSWAY LTD., Jerusalem (IL); THE BOARD OF TRUSTEES OF THE LELAND STANFORD JUNIOR UNIVERSITY, Stanford, CA (US); THE UNITED STATES GOVERNMENT AS REPRESENTED BY THE DEPARTMENT OF VETERANS AFFAIRS, Washington, DC (US)

(72) Inventor: M. Bret Schneider, Portola Valley, CA (US)

(73) Assignees: BRAINSWAY LTD., Jerusalem (IL); THE BOARD OF TRUSTEES OF THE LELAND STANFORD JUNIOR UNIVERSITY, Stanford, CA (US); THE UNITED STATES GOVERNMENT AS REPRESENTED BY THE DEPARTMENT OF VETERANS AFFAIRS, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/874,784

(22) Filed: Jan. 18, 2018

(65) Prior Publication Data

US 2018/0154165 A1 Jun. 7, 2018

Related U.S. Application Data

(63) Continuation of application No. 15/169,564, filed on May 31, 2016, now abandoned, which is a continuation of application No. 13/169,967, filed on Jun. 27, 2011, now Pat. No. 9,352,167, which is a continuation-in-part of application No. 12/324,227, filed on Nov. 26, 2008, now Pat. No. 8,267,850, and a continuation-in-part of application No. 11/429,504, filed on May 5, 2006, now Pat. No. 8,052,591.

(Continued)

(51) Int. Cl.
*A61N 2/02* (2006.01)
*A61N 2/00* (2006.01)

(52) U.S. Cl.
CPC ............... *A61N 2/02* (2013.01); *A61N 2/006* (2013.01); *A61N 2/008* (2013.01)

(58) Field of Classification Search
CPC ........... A61N 2/02; A61N 2/006; A61N 2/008
See application file for complete search history.

(56) References Cited

U.S. PATENT DOCUMENTS 6,537,197 B1* 3/2003 Ruohonen ............... A61N 2/006
335/299
2005/0027284 A1* 2/2005 Lozano ............. A61M 5/14276
604/890.1

* cited by examiner

*Primary Examiner* — Kaylee R Wilson
(74) *Attorney, Agent, or Firm* — Browdy and Neimark, P.L.L.C.

(57) ABSTRACT

Methods of stimulating a target deep brain region using multiple Transcranial Magnetic Stimulation (TMS) electromagnets positioned over a predetermined cortical regions each having a first-order connection to a target deep brain region and applying TMS so that the applied TMS induces spatial summation and thereby modulation of the target deep brain region.

16 Claims, 6 Drawing Sheets

Related U.S. Application Data

(60) Provisional application No. 61/358,847, filed on Jun. 25, 2010.

ENHANCED SPATIAL SUMMATION FOR DEEP-BRAIN TRANSCRANIAL MAGNETIC STIMULATION

CROSS REFERENCE TO RELATED APPLICATIONS

This patent application is a continuation of U.S. patent application Ser. No. 15/169,564, filed on May 31, 2016, titled "ENHANCED SPATIAL SUMMATION FOR DEEP-BRAIN TRANSCRANIAL MAGNETIC STIMULATION," now U.S. Patent Application Publication No. 2017/0113058, which is a continuation of U.S. patent application Ser. No. 13/169,967, filed on Jun. 27, 2011, titled "ENHANCED SPATIAL SUMMATION FOR DEEP-BRAIN TRANSCRANIAL MAGNETIC STIMULATION," now U.S. Pat. No. 9,352,167, which claims priority to U.S. Provisional Patent Application No. 61/358,847, filed on Jun. 25, 2010, and titled "ENHANCED SPATIAL SUMMATION FOR DEEP-BRAIN TRANSCRANIAL MAGNETIC STIMULATION." U.S. patent application Ser. No. 13/169,967 also claims priority as a continuation-in-part of U.S. patent application Ser. No. 12/324,227, filed on Nov. 26, 2008, titled "TRANSCRANIAL MAGNETIC STIMULATION OF DEEP BRAIN TARGETS," now U.S. Pat. No. 8,267,850. U.S. patent application Ser. No. 13/169,967 also claims priority as a continuation-in-part of U.S. patent application Ser. No. 11/429,504, filed on May 5, 2006, titled "TRAJECTORY-BASED DEEP-BRAIN STEREOTACTIC TRANSCRANIAL MAGNETIC STIMULATION," now U.S. Pat. No. 8,052,591.

This patent application may be related to one or more of the following patents and pending patent applications (US and PCT applications), each of which is herein incorporated by reference in its entirety: U.S. Pat. No. 7,520,848, titled "ROBOTIC APPARATUS FOR TARGETING AND PRODUCING DEEP, FOCUSED TRANSCRANIAL MAGNETIC STIMULATION," issued on Apr. 21, 2009; U.S. Pat. No. 8,845,508, titled "ROBOTIC APPARATUS FOR TARGETING AND PRODUCING DEEP, FOCUSED TRANSCRANIAL MAGNETIC STIMULATION," filed on Mar. 11, 2009; U.S. patent application Ser. No. 12/669,882, titled "DEVICE AND METHOD FOR TREATING HYPERTENSION VIA NON-INVASIVE NEUROMODULATION," filed on Jan. 20, 2010, now U.S. Patent Application Publication No. 2010-0256436; U.S. patent application Ser. No. 12/671,260, titled "GANTRY AND SWITCHES FOR POSITION-BASED TRIGGERING OF TMS PULSES IN MOVING COILS," filed on Jan. 29, 2010, now U.S. Patent Application Publication No. 2010-0256439; U.S. patent application Ser. No. 12/670,938, titled "FIRING PATTERNS FOR DEEP BRAIN TRANSCRANIAL MAGNETIC STIMULATION," filed on Jan. 27, 2010, now U.S. Pat. No. 8,956,273; U.S. patent application Ser. No. 12/677,220, titled "FOCUSED MAGNETIC FIELDS", filed on Mar. 9, 2010, now U.S. Patent Application No. 2010/0331602; PCT Application No. PCT/US2008/077851, titled "SYSTEMS AND METHODS FOR COOLING ELECTROMAGNETS FOR TRANSCRANIAL MAGNETIC STIMULATION," filed on Sep. 26, 2008, now Publication No. WO 2009/042863; PCT Application No. PCT/US2008/081048, titled "INTRA-SESSION CONTROL OF TRANSCRANIAL MAGNETIC STIMULATION," filed on Oct. 24, 2008, now Publication No. WO 2009/0556934; PCT Application No. PCT/US2009/045109, titled "TRANSCRANIAL MAGNETIC STIMULATION BY ENHANCED MAGNETIC FIELD PERTURBATIONS," filed on May 26, 2009, now Publication No. WO 2009/143503; U.S. patent application Ser. No. 12/185,544, titled "MONOPHASIC MULTI-COIL ARRAYS FOR TRANSCRANIAL MAGNETIC STIMULATION," filed on Aug. 4, 2008, now U.S. Patent Application Publication No. 2009-0099405; U.S. patent application Ser. No. 12/701,395, titled "CONTROL AND COORDINATION OF TRANSCRANIAL MAGNETIC STIMULATION ELECTROMAGNETS FOR MODULATION OF DEEP BRAIN TARGETS," filed on Feb. 5, 2010, now U.S. Patent Application Publication No. 2010-0185042; and PCT Application No. PCT/US2010/020324, titled "SHAPED COILS FOR TRANSCRANIAL MAGNETIC STIMULATION," filed on Jan. 7, 2010, Publication No. WO 2010/080879.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

Described herein are systems and methods for deep-brain Transcranial Magnetic Stimulation (TMS) of target deep brain regions. Deep-brain TMS may be used to stimulate, enhance or inhibit neural activity in deep-brain target regions for diagnostic and predictive (e.g., treatment formulation) purposes.

BACKGROUND OF THE INVENTION

Transcranial Magnetic Stimulation (TMS) has been used diagnostically for a very long time in velocity of conduction in cortico-spinal tracts and peripheral nerves as well as intra-operative monitoring. For example, see Rossini, P. M. and R. Simone, "Transcranial magnetic stimulation: Diagnostic, therapeutic, and research potential," Neurology, 68:484-488, 2007, which describes the use of TMS for the noninvasive investigation of nerve propagation along the corticospinal tract, spinal roots, and peripheral nerves in humans, including mapping of motor output, and intra-operative monitoring.

Jean-Pascal Lefaucheur and colleagues have examined repetitive Transcranial Magnetic Stimulation (rTMS) of the motor (pre-central) cortex for pain relief (Lefaucheur, J.-P., Drouot, X., Keravel, Y., and J.-P. Nguyen, "Pain relief induced by repetitive transcranial magnetic stimulation of precentral cortex," Neuroreport: 17 Sep. 2001, 12:13, pp. 2963-2965, and Lefaucheur, J.-P., Hatem, S., Nineb, A., Ménard-Lefaucheur, I., Wendling, S., Keravel, Y., and J.-P. Nguyen, "Somatotopic organization of the analgesic effects of motor cortex rTMS in neuropathic pain," Neurology 67:1998-2004, 2006). Lefaucheur ("Use of repetitive transcranial magnetic stimulation in pain relief," Expert Review of Neurotherapeutics, May 2008, Vol. 8, No. 5, Pages 799-808, DOI 10.1586/14737175.8.5.799 (doi: 10.1586/14737175.8.5.799) notes that a subset of patients will get relief from rTMS but relapse and for those patients surgically implanted epidural cortical electrodes and associated pulse generator can be proposed to allow pain relief more permanent, and that the rate of improvement due to rTMS may be predictive of the outcome of such an implantation.

In the early 1990s, Mark George and colleagues described the antidepressant effect of rTMS when applied to the left dorsolateral prefrontal cortex. Since that time, rTMS has become a recognized as an effective method for treating depression. One rTMS device (NeuroStar system by Neuronetics Inc, Malvern, Pa.) has received FDA clearance for marketing for the treatment of depression.

In all of the TMS procedures and devices described above are limited to use of a single coil intended to directly affect a superficial cortical brain region, with unspecified downstream effects within the network. Not surprisingly, the site of primary stimulation on the superficial cortex is typically more affected by rTMS stimulation than are sites which are synaptically connected ("downstream connections) with the primary stimulation site. However, many disorders and symptoms of disorders may benefit from direct neuromodulation of deeper brain target regions. Described herein are devices and methods for deep-brain neuromodulation that may address many of the shortcomings described above.

Deep-brain neuromodulation for therapeutic purposes is well known using either focused (U.S. Pat. No. 7,520,848 and PCT/US2007/010262) or non-focused (U.S. Pat. No. 7,407,478) approaches. However, it remains highly desirable to use TMS for deep-brain neuromodulation in a manner that does not significantly stimulate intervening, non-target regions of the brain (e.g., between the electromagnet(s) and the deep-brain targets). For example, the use of a non-focused TMS electromagnet as described in U.S. Pat. No. 7,407,478 requires higher stimulation at regions of the brain more superficial (e.g., superficial cortical brain regions between the deep brain target and the magnet) than at the deep brain target. We herein propose a solution to this problem by using a specific methodology and device as described herein in order to take advantage of spatial summation of intrinsic brain networks in order to achieve selective deep brain modulation in a manner not previously suggested.

Deep-brain stimulation may be achieved by direct stimulation (e.g., by the direct application of a magnetic field) of the deep brain target, and/or by the indirect stimulation of the deep brain target region by spatial summation at the deep-brain target from more superficial brain regions (including superficial cortical sulci and gyri brain regions near the skull). Described herein are methods including the use of multiple TMS electromagnets that may provide deep-brain stimulation by enhanced spatial summation of resulting in stimulation of one or more deep-brain regions. The deep-brain stimulation described herein may be used in addition to, or in place of, direct deep-brain TMS.

SUMMARY OF THE INVENTION

Described herein are deep-brain TMS systems and methods for diagnosing and/or providing treatment parameters for treatment of a disorder by deep-brain neuromodulation of a patient.

Deep brain stimulation has been notoriously hard to achieve. "Deep brain" stimulation as used herein typically refers to the stimulation of targets within the brain that are located beneath the superficial cortical regions on the outer surface of the brain. Examples of such regions may include the thalamus, cingulate (e.g., anterior cingulate gyms, pregenual cingulate, posterior cingulate gyrus, subgenual cingulate gyrus), putamen, caudate nucleus, hippocampus, ventral striatum, amygdala, subthalamic Nucleus, globus pallidus, and other nuclei of the brain. Thus, deep brain regions may include those regions of the brain which are not immediately adjacent to the skull, but are separated from the skull by one or more intervening structures (e.g., superficial cortical brain structures). Superficial brain regions may include various cortical regions (e.g., motor cortex, somatosensory cortex).

TMS has traditionally had a great deal of trouble stimulating the deeper brain regions at least in part because the applied magnetic field emitted from the magnet falls off so quickly as it passes through the intervening brain regions (e.g., the superficial, cortical, brain regions). Thus, in order to penetrate deeper into the brain, it has typically been thought necessary to increase the power of the applied magnetic field; unfortunately this may result in greater stimulation of the intervening cortical regions, which may result in seizures, pain and other undesired effects.

An alternative method of stimulating deep brain regions may allow a system to take advantage of spatial summation, in which stimulation of two or more brain regions (even superficial cortical regions) may result in targeted and specific stimulation of a deep brain region. Spatial summation as used herein may refer to asynchronous (spaced with sufficient time between pulses such that temporal summation is not effected, for example more than 200 microseconds between onset of successive pulses) or synchronous stimulation of more than one point within a designated brain circuit. Brain circuits comprise electrically or chemically connected groups of brain tissue including neurons and glia, which work together to carry out specific brain functions. Because various points, sometimes called nodes, in a brain circuit are electrically or chemically connected, modulating one site may cause some sort of effect on the other sites in the circuit. Stimulation may typically include both an up-regulation of activity (enhancement) and a down-regulation of activity (e.g., inhibition or depression). For example, for all coil configurations in which multiple brain regions converge on another region, two basic techniques may be employed: (1) synchronous firing of coils and (2) asynchronous firing of the TMS coils. Synchronous firing of coils, particularly when the magnets are fired at powers above motor threshold, may result in synchronous stimulation of multiple points in a brain circuit and may tend to produce long term potentiation (LTP) as described by Bliss and colleagues (enhancement). In general, asynchronous firing of coils, which as used herein may include situations when the timing of the stimulation is far apart in time such that they do not contribute to temporal summation within that circuit, may tend to produce long term depression (LTD), a state of prolonged neural circuit suppression. For example pulses spaced more than 200 microseconds apart from one another when applied to tow or more converging brain regions may result in inhibition at the target deep brain region. This is particularly true if the powers applied at each TMS coil (electromagnet) are low, for example, below motor threshold.

Described herein are methods of producing deep brain stimulation by applying two or more distinct TMS signals to each of two or more distinct brain regions, where the brain regions converge on a deep brain target. In general the deep brain target may be connected to each of the more superficial (e.g., cortical) brain regions by a first-order connection; the connection may be referred to as direct, since the neurons of the more superficial brain region directly connect with (e.g., through a single synaptic connection) the neurons of the deep brain target.

For example, described herein are methods of stimulating a target deep brain region using multiple Transcranial Magnetic Stimulation (TMS) electromagnets. These methods may include the steps of: positioning a first TMS electromagnet over a first predetermined cortical region having a first-order connection to a target deep brain region; positioning a second TMS electromagnet over a second predetermined cortical region having a first-order connection to the target deep brain region; and applying TMS from both the first and second TMS electromagnets so that the applied TMS induces spatial summation of signals received at the target deep brain region from the first and second cortical regions.

This method may therefore allow specific summation at targeted deep brain regions by directing TMS to non-deep brain (e.g., cortical) regions from separately positionable TMS electromagnets. Because the TMS electromagnets may be separately positioned (e.g., independently positioned), they may allow avoidance of stimulation of non-target brain regions (superficial and/or deep) and may also allow the use of more precisely controlled stimulation signals, including lower-power stimulation. For example, in some variations the TMS electromagnets are energized to provide stimulation to the two or more predetermined cortical brain regions that are connected to the target deep brain region by a first order connection at energy levels that do not result in substantial stimulation (including stimulation above motor threshold) at those predetermined cortical brain regions, while causing significant stimulation at the target deep brain region.

Any appropriate number of TMS electromagnets may be used. For example, in some variations the method further comprises positioning a third TMS electromagnet over a third cortical region having a first-order connection to the target deep brain region; for or more independently positionable TMS electromagnets may be used.

In general, any appropriate TMS electromagnet may be used, however because of size and spacing constraints, it may be beneficial to use TMS electromagnets that have a swept-back or V-shaped configuration, with a vertex region configured to be positioned near the subject's head. Such magnets may therefore be modified figure-8 type coils ("traditional TMS coils") which are bent or curved, e.g. as described in PCT Application No. PCT/US2010/020324, titled "SHAPED COILS FOR TRANSCRANIAL MAGNETIC STIMULATION", and in several of the other patent applications previously incorporated by reference.

As mentioned above, any appropriate predetermined cortical region having a first-order connection to the target deep brain region may be chosen. The examples provided below illustrate some of these cortical regions and their first-order connections. Such cortical brain regions and first order connections may be chosen from among those that are well-known in the literature, or they may be determined using one of the methods described herein. For example a first-order (e.g., direct) connection between a cortical or superficial brain region and a target deep brain region may be determined using anatomical markers; a cortical brain region may exhibit connections (e.g., synaptic connections off of dendritic or axonal extensions) onto axons, axonal bundles, dendritic arbors, or the other projections extending from the cell bodies of the neurons (or onto the cell bodies themselves) forming the deep brain target. Thus, although the superficial, cortical brain region may be anatomically separated from the deep brain target by a significant distance, the cells (e.g., neurons, glia, etc.) forming each of the regions are typically directly connected to each other. Direct connections may therefore be identified from atlases of neuroanatomy, or by imaging or dye-injection/tracing techniques that are well-known in the art. In some variations, direct connections may be identified using the devices described herein by applying stimulation to a predetermined cortical region at various (e.g., increasing) levels of stimulation and imaging to determine what (if any) deep brain regions receive downstream input (which may be imaged by PET or other activity/metabolic determining scans).

The signals applied to the various predetermined cortical regions may be adjusted to prevent substantial simulation of adjacent cortical regions, or may be limited from stimulating adjacent regions. The TMS electromagnet may be configured to emit a focused or limited field. In addition, the net direction of the field emitted by the electromagnet may be controlled to direct stimulation as desired In some variations, the TMS applied to all of the predetermined cortical regions may by the various independent TMS electromagnets may be coordinated (e.g., simultaneous or delayed by a predetermined amount). For example, the step of applying TMS to the various tissue regions may include synchronizing the applied TMS from the first and second TMS electromagnets.

As mentioned, in general independent TMS electromagnets may be positioned in separate locations around the subject's head. For example, positioning the first and second TMS electromagnets may comprise positioning discrete one coil or two coil TMS electromagnets. Thus, the step of applying TMS may comprise applying TMS only locally to the predetermined cortical regions, rather than the entire brain.

In some variations, the method may also include directly stimulation the deep brain region concurrent with stimulation by spatial summation. For example, the method may include directly stimulating the deep brain target using TMS (e.g., by targeting a plurality of TMS electromagnets at the deep brain region) concurrent with the TMS of the first and second cortical brain regions (or more) as discussed above.

Any of the methods of treating a patient described herein may be used to treat a patient for a medical disorder, including treating a patient for depression, addiction, or pain. The method of treatment for any specific disorder may be related to a particular deep brain target. Exemplary deep brain targets may include one or more of: thalamus, cingulate, putamen, caudate nucleus, hippocampus, ventral striatum, and amygdala.

For example, described herein are methods of treating a patient for a disorder by stimulating a target deep brain region using multiple Transcranial Magnetic Stimulation (TMS) electromagnets to induce spatial summation from various cortical regions at the target deep brain region. A method of treatment may include the steps of: positioning a plurality of discrete TMS electromagnets over a plurality of predetermined cortical regions each having a first-order connection to a target deep brain region, so that each TMS electromagnet can apply TMS to one of the predetermined cortical regions; and treating the patient by applying TMS from the plurality of TMS electromagnets so that the applied TMS induces spatial summation of signals received at the deep brain region from the plurality of cortical regions.

DETAILED DESCRIPTION OF THE INVENTION

Included herein are systems and methods for modulating deep brain target regions using a plurality of (e.g., an array of) TMS electromagnets arranged in predetermined regions around the patient's head in order to reliably trigger deep brain stimulation. Deep-brain neuromodulation using multiple-electromagnet arrays may be accomplished using a variation of stereotactic Transcranial Magnetic Stimulation (sTMS) (see, e.g., PCT/US2007/010262, previously incorporated by reference), as described herein. The deep-brain stimulation described herein may result from spatial summation of superficial cortical primary stimulation sites, from direct stimulation of the deep-brain target by the applied magnetic field, or by a combination of the direct stimulation (which may sensitize, excite/inhibit, etc.) and indirect (spatial summation as described in the context of the present invention).

Figure 1:
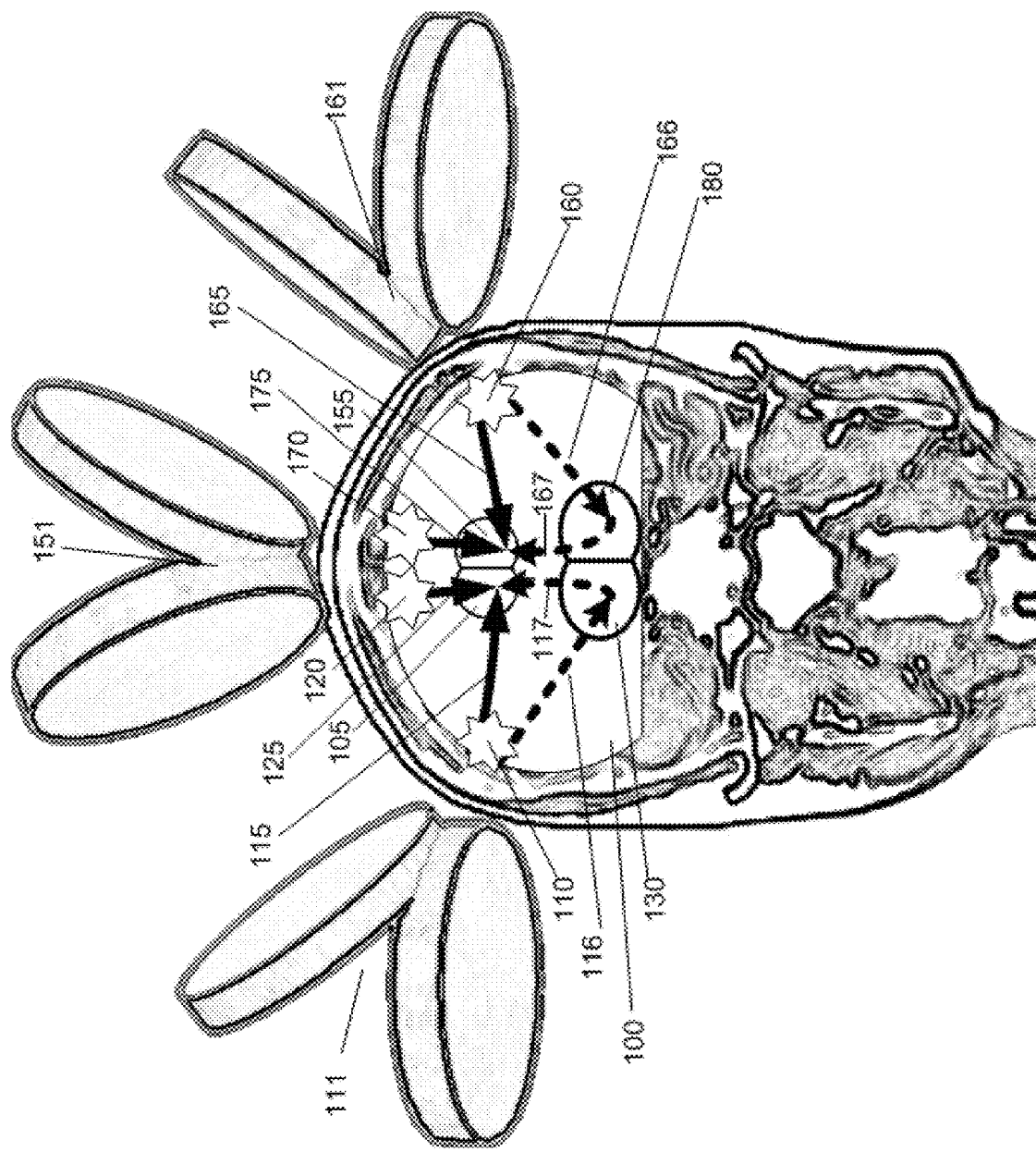
FIG. 1 illustrates general aspects of the present invention in an example in which three TMS electromagnets in a configuration targeting the Cingulate Gyrus (CG).

FIG. 1 illustrates an sTMS system including three sTMS electromagnets (though two, four, or more magnets may be included) that are used for deep-brain neuromodulation. The electromagnet coils may be driven by one or more stimulators. For example, the TMS electromagnets may be driven by multiple Magstim Rapid2 stimulators that are simultaneously triggered, or by a single such stimulator with output current divided between the multiple coils in parallel, in series, or in series-parallel. In such an embodiment, regulation of the current going through each individual coil may be achieved in such an embodiment by resistive or inductive strategies.

In FIG. 1, the target deep-brain region is stimulated. Stimulation of the deep-brain target (e.g. CG) by the plurality of TMS electromagnets has been verified by PET scan. In FIG. 1, the plurality of TMS electromagnets apply energy that results in signals being sent from more superficially-located regions (e.g., nearer the magnets) along (anatomical) neural pathways such as white matter fiber tracts, to the target region. In this example, each TMS electromagnet is fired at nearly the same time (temporally synchronized) and delivered from multiple separate regions of primary stimulation around the brain cortical surface, such that the signals converge on the deep-brain target, for example via intrinsic white matter pathways. Although the deep-brain target may also be modulated (e.g., stimulated) directly by one or a combined magnetic field(s) of the TMS electromagnets, at least some of the neuromodulation occurs by spatial summation of primary stimulation sites located in regions located superficial to the deeper target zone.

In FIG. 1, the figure illustrates the following elements:
100 Brain
105 Patient's right anterior cingulate
130 Patient's right thalamus
116 Patient's right (frontal) cortico-thalamic connection
117 Right thalamo-cingulate connection
110 Right primary site of stimulation
111 Right lateral TMS coil
115 Right (frontal) cortico-cingulate connection B
125 Right (frontal) cortico-cingulate connection A
151 Superior TMS coil
170 Left superior primary site of stimulation
175 Left (frontal) cortico-cingulate connection A
155 Patient's left anterior cingulate
165 Left cortico-cingulate connection B
160 Left Primary site of stimulation
161 Left lateral TMS coil
166 Left cortico-thalamic connection
167 Left thalamo-cingulate connection As mentioned, FIG. 1 illustrates one mechanism by which the plurality of TMS coils may be reaching the deep-brain target, e.g., anterior cingulate gyrus (ACG). In this example, spatial summation occurs because the plurality of coils each fire, resulting in modulation of superficial regions that is carried by anatomical interconnections between the neurons, ultimately modulating the deep-brain target. In some variations, the deep brain target may also be directly modulated by one or more (or by a combined signal from) the TMS coils. The more superficial regions may transmit a signal (e.g., an excitatory neural signal) to the deep-brain target directly or via one or more intermediate connections. For example, in FIG. 1, signals from the more superficial regions are relayed through the thalamus and on to the ACG. Each TMS coils (magnet) may be controlled independently, even when fired synchronously. Thus different power levels, frequencies of stimulation, and superficial targets maybe used. Controlling each TMS coil separately may allow more precise targeting and modulation of the deep-brain regions. Alternatively, in some variations, two or more (including all) of the TMS coils may be powered and controlled together as described above. (Frontal) cortico-cingulate connections 115, 116, 165 and 175 are examples of known cingulate white matter tracts which have been documented in the scientific literature including, for example, in Yu C, Lin F, Li K, Jiang T, Qin W, Sun H, Chan P., "Pathogenesis of normal-appearing white matter damage in neuromyelitis optica: diffusion-tensor MR imaging" (Radiology. 2008 January; 246(1)).

Because multiple inputs to designated circuit are input to a targeted network, the extent of the modulation of downstream deep regions is greater than that which would occur with only a single point of superficial stimulation input. This result is related to spatial summation of at the target brain region. Spatial summation in the sense it is used here typically refers to the convergence of signals from multiple parallel sources, in this case neurons or bundles of neuronal white matter, also known as tracts. By having multiple magnets, precise physical placement of each stimulation source can be achieved, thus allowing one to focally control (precisely control) the which groups of cortical neurons receive primary (direct) stimulation. Individual control of the power and pulse rate of each coil may thus permit the precise control of input into the network, and stimulation at the target.

Although FIG. 1 illustrates a simplified variation showing two nerve tracts, multiple pathways (including individual nerves or nerve bundles/tracts), can cooperatively serve as vehicles to facilitate the modulation of the deep brain target based on the application of TMS in accordance with the method and device described.

In the example shown in FIG. 1, the primary site of stimulation is more superficial (e.g., superficial cortical). The native connections inside of the brain pass on the stimulation to the deep-brain region. The arrows illustrate these connections (e.g., fiber bundles) that may be present. In the case of the upper solid arrows, stimulation is passed directly to the cinguate. An indirect route is shown (160, 180) at the bottom, in which the signal is detoured through the thalamus, as mentioned above. Cortical stimulation may be used to relay signal(s) to the deep brain target. In this example, the multiple magnets may be independently controlled, as mentioned above.

Figure 2:
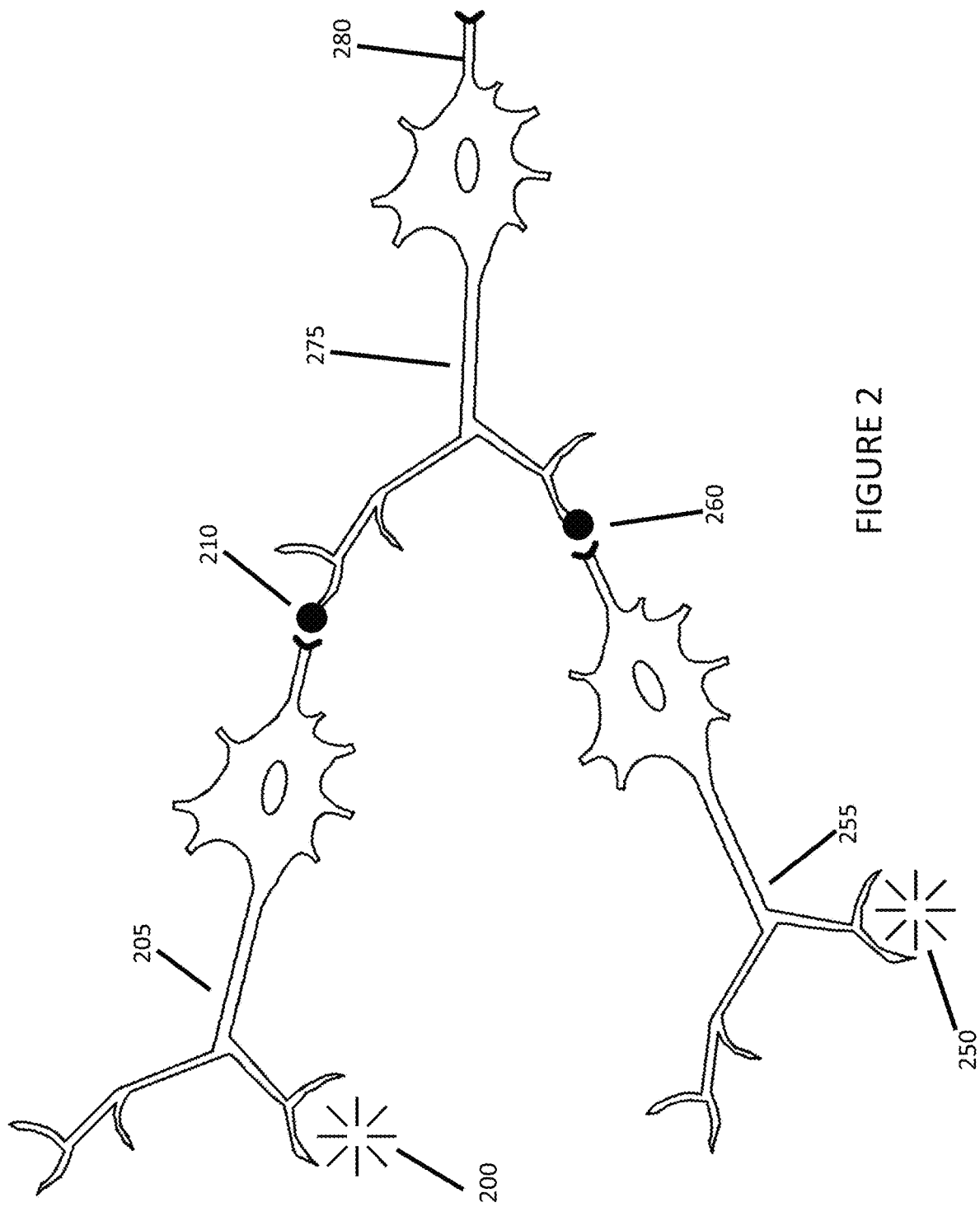
FIG. 2 is a simplified exemplary neuronal network showing spatial summation.

FIG. 2 illustrates on example of a network of neurons that may demonstrate spatial summation. The elements are described below include:

200 Point of Primary Stimulation
205 Neural Input
210 Synapse
250 Point of Primary Stimulation
255 Neural Input
260 Synapse
275 Convergence
280 Spatial Summation Effect Although other examples of cellular spatial summation have been described (see, e.g., Chapter 12, "Synaptic Integration," in *Principles of Neural Science*, by Kandel, Schwartz and Jessell, $4^{th}$ Edition, McGraw-Hill 2000 pp 23-24), this concept has not been previously applied to TMS stimulation, in part because of the perceived complexity and difficulty controlling the final stimulation at the deep brain target. The methods described herein may allow for controlled deep brain stimulation by spatial summation from more superficial (e.g., superficial cortical) regions, when modulation of a deep brain target is intended.

Figure 3A:
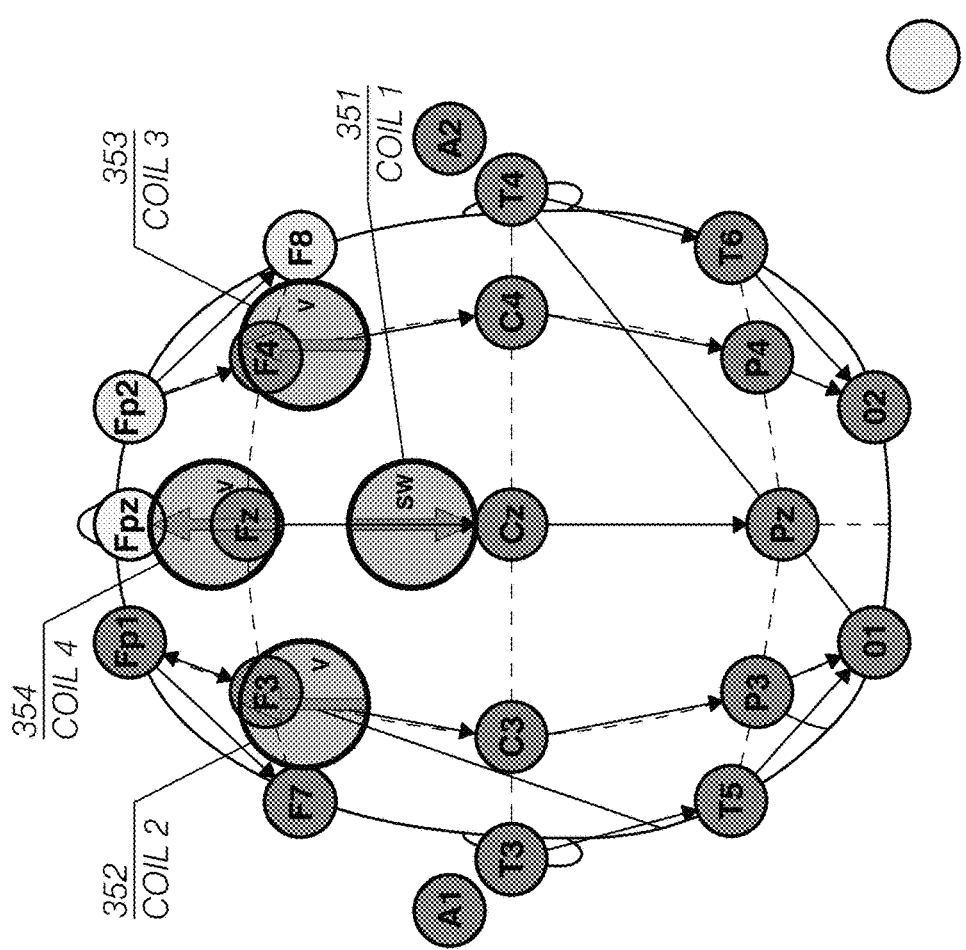
FIG. 3A illustrates one configuration of TMS electromagnets which may be used to target stimulation of the dorsal anterior cingulate gyrus.
Figure 3B:
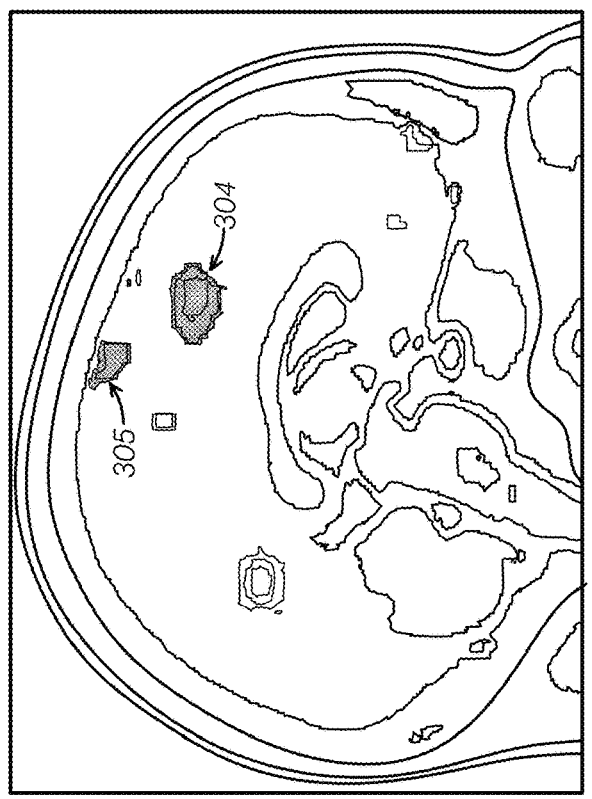
FIG. 3B shows an exemplary PET scan of a patient's brain, indicating suppression at the dorsal anterior cingulate when using the configuration of FIG. 3A to modulate (stimulate) the deep brain target.

FIGS. 3A and 3B illustrate another variation of a method of targeting the dorsal anterior cingulate gyrus via spatial summation as discussed above. Functioning within the context of the paradigm shown in these figures are known neural connections that tie the white matter of the anterior cingulate to BA 8 and BA 46 regions (as illustrated as connections 124, 175, 115 and 165) are shown previously in FIG. 1. These known neural connections have been documented in the scientific literature including, for example, in Yu C, Lin F, Li K, Jiang T, Qin W, Sun H, Chan P., "Pathogenesis of normal-appearing white matter damage in neuromyelitis optica: diffusion-tensor MR imaging" (Radiology. 2008 January; 246(1)).

FIG. 3A schematically shows one configuration of TMS electromagnets arranged to target superficial cortical regions connected by first-order connections to the dorsal anterior cingulate gyrus. The placement of these coils is shown with respect to a map of the superficial cortical locations marked by the standard "EEG 10-20" positioning system. This configuration may be referred to as the "NeoStim NS-4A" configuration or array, and may be useful for targeting dorsal anterior cingulate gyrus via spatial summation. Referring to FIG. 3B, in this configuration, COIL 1 351 is positioned anterior to the position of Cz, which is known to lie above a brain region known as Brodmann's Area 8, or "BA8". This TMS electromagnet has the primary current of the coil moving down and anteriorly, relative in the figure, as indicated by the direction of the arrow within. COIL 2 352 left is positioned near F3 (e.g., over BA 9/46), and the primary current of the coil is shown moving anteriorly. COIL 3 353 right is positioned near F4 (over BA 9/46), and the primary current of coil is shown moving anteriorly. Finally, COIL 4 354 is positioned near Fz (over BA 10), and the primary current of coil moving posteriorly Using the configuration of four TMS electromagnets shown in FIG. 3A, the targeted superficial regions may be stimulated by synchronously or asynchronously (greater than 200 microseconds between onset of each pulse) applying energy to each of the four target regions, resulting in a modulation of the deep brain target. In practice, this modulation may be visualized and confirmed using a PET scan, which can reflect brain activity. FIG. 3B shows a PET scan of a subject's brain after treatment using the configuration of TMS electromagnets shown in FIG. 3A, and shows (by highlighted regions of the scan 304) suppression at the dorsal anterior cingulate region which exceed suppression on frontal cortical surface 305.

Figure 4A:
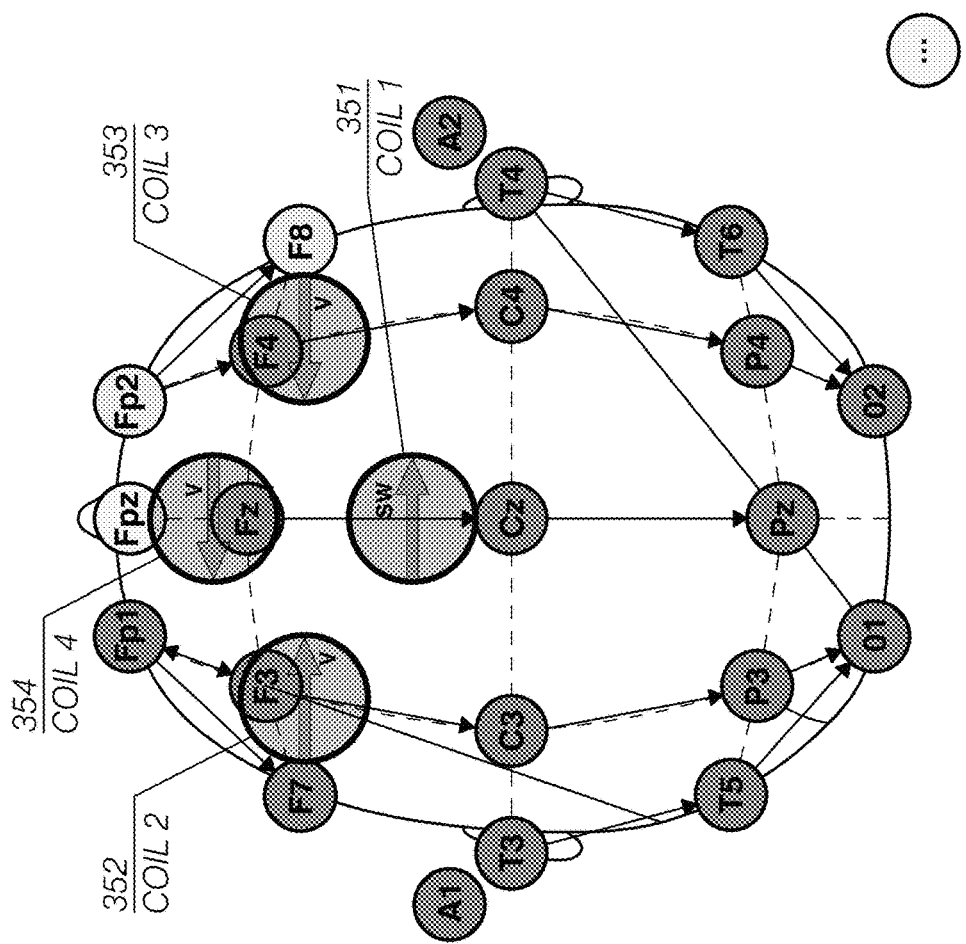
FIGS. 4A and 4B illustrate another exemplary configuration (FIG. 4A) and resultant PET scan (FIG. 4B) in which the deep brain target is the pre-genual and subgenual (aka subcollosal) areas of the anterior cingulate.
Figure 4B:
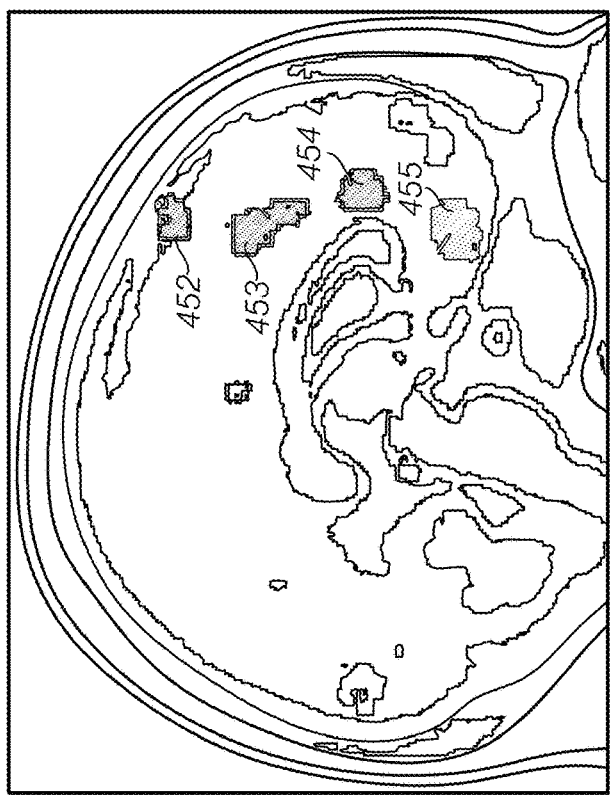

FIGS. 4A and 4B illustrate another example. In this example, the pre-genual and subgenual (aka subcollosal) areas of the anterior cingulate are targeted via spatial summation, as illustrated in FIG. 4A. FIG. 4A shows another 4-coil array (which may be referred to as "NeoStim NS-4B") in which four TMS coils are placed in specific locations and orientations (with respect to a standard EEG 10-20 map of the scalp) on the head as shown in FIG. 4A: COIL 1 351 is positioned anterior to Cz (e.g., over BA8), and the primary current of the coil is shown moving to right; COIL 2 352 left is positioned near F3 (e.g., over BA 9/46), and the primary current of coil is shown moving up; COIL 3 353 right is positioned near F4 (e.g., over BA 9/46), and the primary current of coil is shown moving up; and COIL 4 354 is positioned near Fz (e.g., over BA 10), and the primary current of coil moving to left.

FIG. 4B shows a PET scan of a subject stimulated with this configuration of TMS electromagnets. In the exemplary scan, the pre-genual area 454 shows decreased evidence of decreased activity and subgenual (aka subcollosal) area 455 shows evidence of increased activity in response to the stimulation. Also observed in this image are signs of decreased in activity in the dorsal cingulate 453 and frontal cortical surface 452.

Figure 5A:
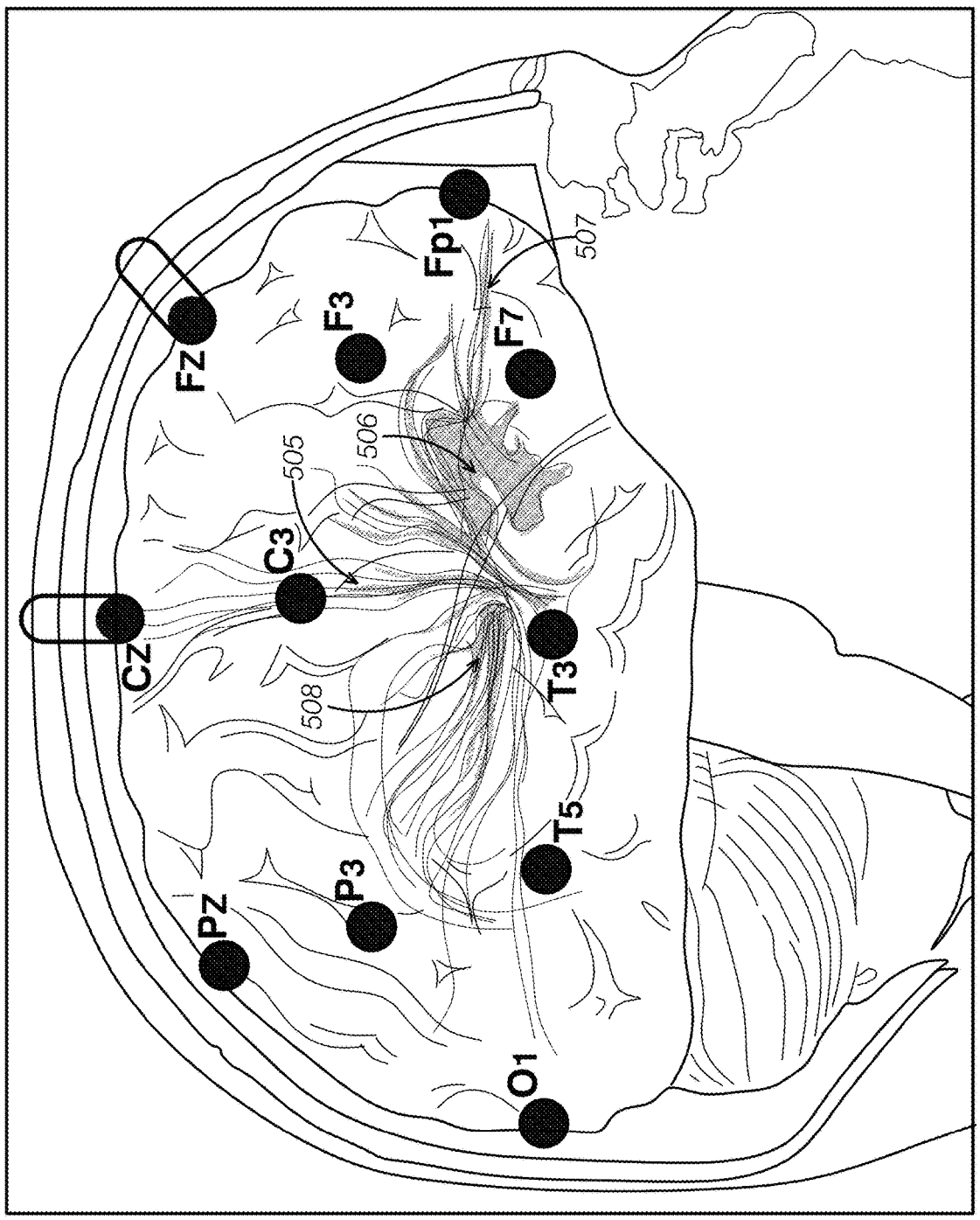
FIGS. 5A and 5B show side and top sections through a model of a brain indicating first order connections between various superficial cortical regions and the right anterior insula (a deep brain target).
Figure 5B:
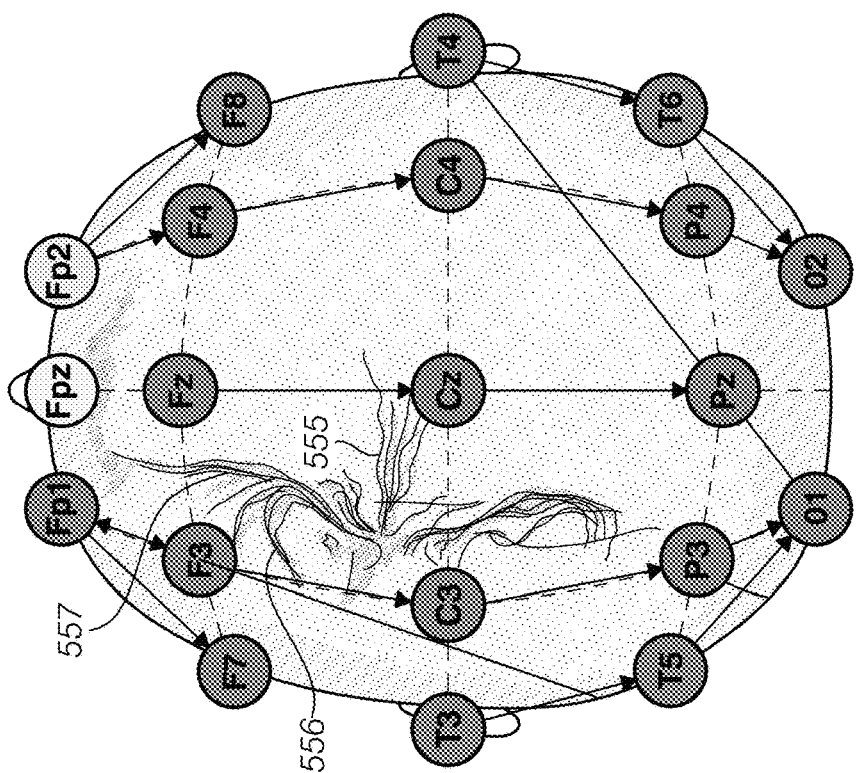

FIGS. 5A and 5B shows side and top views of a patient's head, and illustrates the first-order connection between various superficial cortical regions and the target deep brain region. In this example, the target deep brain region is the right anterior insula. Thus, by providing TMS stimulation targeting these specific and discrete superficial cortical regions, spatial summation may allow the target deep brain regions to be stimulated as desired. Internal capsule tract 505 connects the anterior cingulate with premotor areas of the cortex, and may be influenced by stimulating BA 8, under Cz, and also under C3. Uncinate fasciculus 506 connects low lateral frontal lobe regions to the anterior cingulate, and may be influenced by stimulating beneath BA 44, 45 and 46. Subfrontal tract 507 connects the anterior insula to the orbitofrontal cortex, and may be influenced by stimulating over BA 10. Posterior motor tract 508 also connects into the insula, but is an insula input which in many cases should be avoided when attempted to stimulate the insula because in primary contributes to the posterior insula, and its connections to the motor cortex could increase the potential for stimulation of this area to lead to seizure. In the axial (top-down) view shown in FIG. 5B, 556 is the same as 506 in FIG. 5A, 557 is the same as 507, and 55 is the same as 505. In FIG. 5B, the tracts associated with the left insula are shown, but are intended to be illustrative of the essentially identical tracts of the right insula.

Figure 6:
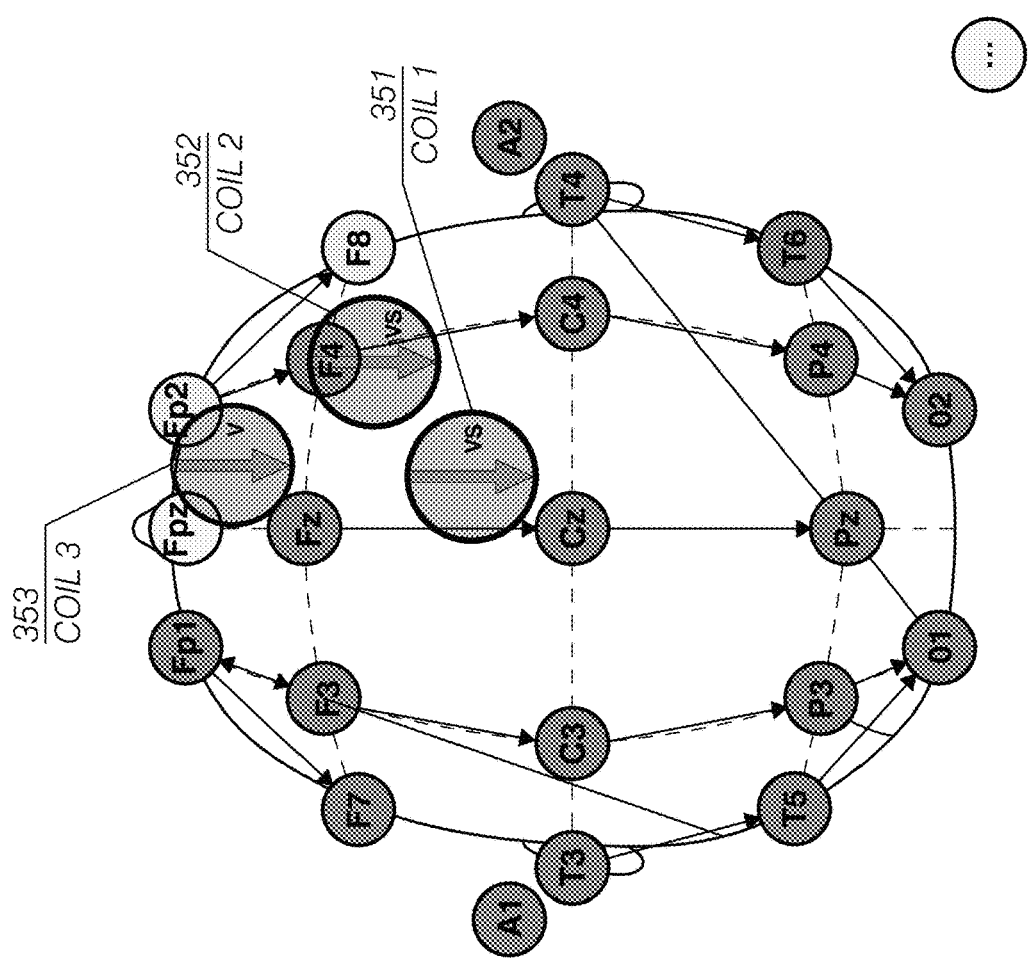
FIG. 6 illustrates one configuration of TMS electromagnets which may be used to target stimulation of the right anterior insula.

For example, as illustrated in FIG. 6, an array of three TMS electromagnets may be positioned and used to modulate the right anterior insula.

For example, COIL 1 351 right is shown positioned anterior to Cz, e.g., over BA8 and the insula white matter tracts 505 which extend through the internal capsule to premotor areas of the brain. COIL 2 352 left is positioned posterior to F3, e.g., over BA 44,45 if this position can be tolerated by patient; but frequently it is not tolerable due to the location of temporalis muscle and auriculotermporal and zygomaticotemporal branches of the trigeminal nerve. As a practical compromise with good utility, pair resulting from stimulation of the temporalis and associated nerves may be approached by slightly displacing the TMS coil/electromagnet superiorly, over BA46. This region also includes the white matter fibers of the uncinate fasciculus, which is an integral part of the insula. Finally, COIL 3 353 right is positioned between Fz, Fpz, and Fp2 (over BA10, and white matter tracts which connect the anterior insula to the orbitofrontal tract, including the median forebrain bundle).

As mentioned, any of these variations, including those above describes, may include positioning the plurality of TMS electromagnets from outside of the subject's head to drive modulation of a deep brain target by stimulating the more superficial cortical regions that have a first order, direct connection to the desired deep brain target.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. Such modifications and changes do not depart from the true spirit and scope of the present invention.

What is claimed is:

1. A method of stimulating a target deep brain region, the method comprising:
    positioning a first Transcranial Magnetic Stimulation (TMS) electromagnetic over a first predetermined cortical region having a first-order connection to the target deep brain region;
    positioning a second TMS electromagnetic over a second predetermined cortical region having a first-order connection to the target deep brain region;
    stimulating the first and second predetermined cortical regions by applying TMS from both the first and second TMS electromagnets; and
    stimulating the target deep brain region by spatial summation of signals received at the target deep brain region from the stimulated first and second predetermined cortical regions.

2. The method of claim 1, further comprising positioning a third TMS electromagnet over a third predetermined cortical region having a first-order connection to the target deep brain region.

3. The method of claim 1, wherein the step of applying TMS comprises synchronizing the applied TMS from the first and second TMS electromagnets.

4. The method of claim 1, wherein the step of positioning the first and second TMS electromagnets comprises positioning discrete one coil or two coil TMS electromagnets.

5. The method of claim 1, wherein the step of applying TMS comprises applying TMS only locally to the predetermined cortical regions, rather than the entire brain.

6. The method of claim 1, further comprising directly stimulating the target deep brain region concurrent with the TMS of the first and second predetermined cortical brain regions.

7. The method of claim 1, further comprising treating a patient for depression, addiction, or pain.

8. The method of claim 1, wherein the target deep brain region comprises one of: thalamus, cingulate, putamen, caudate nucleus, hippocampus, ventral striatum, and amygdala.

9. A method of treating a patient for a disorder by stimulating a target deep brain region, the method comprising:
    positioning a plurality of discrete Transcranial Magnetic Stimulation (TMS) electromagnets over a plurality of predetermined cortical regions each having a first-order connection to a target deep brain region;
    stimulating each of the plurality of predetermined cortical regions by applying TMS to each of the plurality of predetermined cortical regions from each corresponding TMS electromagnet; and
    treating the patient by receiving spatial summation of signals at the deep brain region received from the plurality of predetermined cortical regions.

10. The method of claim 9, wherein the treating comprises synchronizing the applied TMS from the plurality of TMS electromagnets.

11. The method of claim 9, wherein positioning comprises positioning a first TMS electromagnet coil and a second TMS electromagnet coil.

12. The method of claim 9, wherein treating comprises applying TMS only locally to the predetermined cortical regions, rather than the entire brain.

13. The method of claim 9, further comprising directly stimulating the target deep brain region concurrent with the TMS of the predetermined cortical regions.

14. The method of claim 9, wherein treating comprises treating the patient for depression, addiction, or pain.

15. The method of claim 9, wherein the target deep brain region comprises one of: thalamus, cingulate, putamen, caudate nucleus, hippocampus, ventral striatum, and amygdala.

16. The method of claim 9, wherein treating the patient by receiving spatial summation of signals at the deep brain region received from the plurality of predetermined cortical regions includes stimulating the deep brain region by spatial summation of signals received at the deep brain region from stimulating each of the plurality of predetermined cortical regions.

* * * * *